United States Patent [19]

Wu et al.

[11] Patent Number: 6,040,915
[45] Date of Patent: Mar. 21, 2000

[54] ANALYSIS METHOD FOR GASES AND APPARATUS THEREFOR

[75] Inventors: Shang-Qian Wu; Jun-ichi Morishita; Yoshio Ishihara; Tetsuya Kimijima, all of Tokyo, Japan

[73] Assignee: Nippon Sanso Corporation, Tokyo, Japan

[21] Appl. No.: 09/147,349

[22] PCT Filed: Apr. 8, 1998

[86] PCT No.: PCT/JP98/01608

§ 371 Date: Dec. 7, 1998

§ 102(e) Date: Dec. 7, 1998

[87] PCT Pub. No.: WO98/45686

PCT Pub. Date: Oct. 15, 1998

[30] Foreign Application Priority Data

Apr. 9, 1997 [JP] Japan .................................. 9-091158

[51] Int. Cl.[7] .................................................. G01N 21/61
[52] U.S. Cl. .......................................... 356/435; 250/345
[58] Field of Search .................................. 356/435, 437; 250/345

[56] References Cited

U.S. PATENT DOCUMENTS

| | | | |
|---|---|---|---|
| 4,042,304 | 8/1977 | Martin et al. ........................... | 356/128 |
| 4,180,733 | 12/1979 | Veda ...................................... | 250/345 |
| 4,256,964 | 3/1981 | Ishida et al. .......................... | 250/345 |
| 4,803,052 | 2/1989 | Abromaitis et al. ................... | 250/345 |
| 4,990,780 | 2/1991 | Lee et al. .............................. | 250/343 |
| 5,703,365 | 12/1997 | Ishihara et al. . | |

*Primary Examiner*—Richard A. Rosenberger
*Attorney, Agent, or Firm*—Oblon, Spivak, McClelland, Maier & Neustadt, P.C.

[57] ABSTRACT

A method for analyzing an impurity in a gas including the steps of: introducing a gas with an impurity into a first cell; introducing a gas with no impurity into a second cell; maintaining identical pressures in the first and second cells; irradiating a light from a light irradiating source; varying the frequency of the light over a frequency spectrum including an absorption frequency of the impurity; splitting the light by a splitting device in order to pass a first beam through the first cell and to pass a second beam through the second cell; measuring the intensity of the light passing through the first cell over the frequency spectrum with a first measuring device and the intensity of the light passing through the second cell over the frequency spectrum with a second measuring device; and determining an absorption spectrum of the impurity in the gas based on the difference between data measured with the first measuring device and data from measured with the second measuring device.

22 Claims, 15 Drawing Sheets

ANALYSIS METHOD FOR GASES AND APPARATUS THEREFOR

TECHNICAL FIELD

The present invention relates to a method and to an apparatus for analyzing trace amounts of components in a gas to be measured by means of optical absorption spectroscopic analysis employing a semiconductor laser as the light source, and in particular relates to a method and to an apparatus for analyzing trace impurity concentrations, such as $H_2O$, in a matrix gas by eliminating interference absorption due to a gas, such as ammonia and silane, having absorption spectra in the near infrared region, with high sensitivity and accuracy in a real-time manner.

This application is based on Japanese Patent Application No. Hei 9-91158, the contents of which are incorporated herein by reference.

BACKGROUND ART

Various kinds of spectroscopic analysis using a semiconductor laser as the light source have been used. The characteristics common to analysis in the prior art are that a matrix gas must be transparent at wavelengths of the light source and that the intensity of the light may be attenuated by absorption by impurity molecules to be measured. With the analysis of the prior art, identification of trace amounts of an impurity can be made from the difference between absorption intensities (amounts of absorption) of a matrix gas and a target impurity, at identical wavelengths.

However, most gas molecules have overtone absorption bands and combination tone absorption band in the near infrared wavelength region. When both the matrix gas and the target impurity to be measured absorb light at identical wavelengths and the amount of optical absorption by the matrix gas is greater than that by the target impurity, the resolution and the accuracy of the measurement decrease because of interference absorption.

There was also a problem in that noise from the light source must be decreased in order to improve detection sensitivity. In the prior art, a dual beam measurement method is employed to decrease the noise. However, with this method, only the noise from the light source can be eliminated whereas influences due to the interference absorption arising from the matrix gas and to absorption arising from the target impurity in a purge box (out of a cell) cannot be eliminated.

There are two methods to eliminate noise in the dual beam measurement method of the prior art. In one conventional method, powers of beams reaching two light detectors are adjusted to be balanced, photoelectric conversion is carried out, and noise is thereafter cancelled with a differential amplifier. In another conventional method, by amplified gains from current/voltage conversion preamplifiers, which are provided after light detectors and before lock-in amplifiers, are adjusted so that outputs from the preamplifiers in two channels are balanced, and noise is thereafter cancelled by a differential amplifier. With these methods, noise cannot be completely removed and the adjustment for the apparatus is complicated because these methods make control of analog signals in a time domain delicate.

FIG. 3 shows an example of an analysis apparatus of the prior art, which comprises a semiconductor laser 1 (a light source), a collimating lens 11, a half mirror 12, a mirror 13, a light splitting means 4 for splitting light from the semiconductor laser 1 into two beams, a sample cell 2 through which a split beam passes, a first detector 5 for measuring an intensity of the beam, a second detector 6 through which the other split beam passes, first and second lock-in amplifiers 21 and 22, first and second AD converters 23 and 24 which are connected to the first and second lock-in amplifiers 21 and 22, and a computer 25 for identifying a trace impurity concentration in the matrix gas in the sample cell 2. A laser current driver 1a drives the semiconductor laser 1 and a gas supply means 9 introduces and exhausts the matrix gas into and from the sample cell 2.

FIGS. 4 to 7 show the result of the measurement using the analysis apparatus of the prior art. FIG. 4 shows absorption spectra of $NH_3$ and $H_2O$ around a wavelength of 1.37 µm, and FIG. 5 shows absorption spectra of $SiH_4$ and $H_2O$ around a wavelength of 1.38 µm. As seen from FIGS. 4 and 5, the measurements for trace moisture concentrations in $NH_3$ and $SiH_4$ interfere with the absorption spectra of $NH_3$ and $SiH_4$.

FIG. 6 shows spectra obtained by measurement in the case where $H_2O$ is added to the $NH_3$ gas, and FIG. 7 shows a calibration curve obtained from the result of the measurement of FIG. 6. It is obvious from FIG. 7 that the absorption spectrum peak corresponding to the concentration of $H_2O$ is not linearly varied because of the interference absorption of $NH_3$.

With the analysis method of the prior art, the influences due to the interference absorption arising from the matrix gas and to absorption arising from the target impurity in a purge box (out of a cell), cannot be eliminated. As a result, it is increasingly demanded that the influences from the interference absorption of the matrix gas, from the noise of the light source, and from the absorption of the target impurity in the purge box (out of the cell), be simultaneously removed in identification of impurities in gas having interference absorption, such as $NH_3$ and $SiH_4$, with high sensitivity and accuracy.

DISCLOSURE OF INVENTION

It is therefore an object of the present invention to provide a method and an apparatus for analyzing a trace impurity concentration, eliminating interference absorption with high sensitivity and accuracy.

In order to accomplish the above object, a method for analyzing an impurity in a gas, according to the present invention, comprises the steps of: introducing a gas with an impurity into a first cell; introducing a gas with no impurity into a second cell; maintaining identical pressures in the first and second cells; irradiating a light from a light irradiating means; splitting the light by a splitting means in order to pass a first beam through the first cell and to pass a second beam through the second cell; measuring the intensity of the light passing through the first cell by a first measuring means and the intensity of the light passing through the second cell by a second measuring means; and determining an absorption spectrum of the impurity in the gas based on the difference between measuring data from the first measuring means and measuring data from the second measuring means.

By measuring the absorption of the impurity based on the difference between the absorption (absorption of the impurity and absorption of the matrix gas) in the first cell and the absorption (absorption of the matrix gas) in the second cell, impurities such as $H_2O$ in a gas such as $NH_3$ or $SiH_4$ having interference absorption can be identified with high sensitivity and accuracy.

In another aspect of the present invention, a first light path from the splitting means via the first cell to the first measuring means and a second light path from the splitting means via the second cell to the second measuring means may have identical optical characteristics, and the pressures and the flow rates in the first cell and the second cell may be equalized, so that the background absorption in the both light paths become identical and the difference between the absorption at the first light path and the absorption at the second light path coincides with the absorption by the impurity, thereby enhancing the sensitivity in the identification of the impurity.

In another aspect of the present invention, the outputs from the first and second light paths may be simultaneously converted into digital signals at every measured wavelength region, the measuring data from the second light path may be multiplied by a coefficient corresponding to the light power ratio of the second and second laser beams, and the measuring data from the first measuring means is subtracted from the measuring data of the first measuring means, so that the absorption spectrum of the target impurity is accurately measured and the trace impurity can be identified.

In another aspect of the present invention, the optical system may be enclosed with a gas substantially having no absorption in the measured wavelength. The laser beams passing from the light irradiating means to the first and second measuring means are prevented from being attenuated due to moisture etc., in the air, and the measurement for an impurity of a component such as moisture in the air can therefore be carried out with high sensitivity.

In another aspect of the present invention, the first light path length may be adjusted to be equal to the second light path length, thereby equalizing the attenuation and luminous intensities of the laser beams and improving detection sensitivity.

An analysis apparatus for analyzing an impurity in a gas, according to the present invention, comprises: light irradiating means; a first cell into which a gas with an impurity to be measured is introduced; a second cell into which a gas with no impurity is introduced; splitting means for splitting the light from the light irradiating means in order to pass a first beam through the first cell and to pass a second beam through the second cell; first measuring means for measuring the intensity of the first beam passing through the first cell; second measuring means for measuring the intensity of the second beam passing through the second cell; gas supply means for supplying the gas with the impurity to the first cell and the gas with no impurity into the second cell while maintaining identical pressures in the first and second cells; and determination means for determining an absorption spectrum of the impurity in the gas based on the difference between measuring data from the first measuring means and measuring data from the second measuring means.

By measuring the absorption of the impurity based on the difference between the absorption (absorption of the impurity and absorption of the matrix gas) in the first cell and the absorption (absorption of the matrix gas) in the second cell, impurities such a as $H_2O$ in a gas such as $NH_3$ or $SiH_4$ having the interference absorption can be identified with high sensitivity and accuracy.

In another aspect of the present invention, the first light path and the second light path may have identical optical characteristics, and the pressures and the flow rates in the first cell and the second cell may be equalized. The outputs from the first and second light paths may be simultaneously converted into digital signals at every measured wavelength region. The measuring data from the second light path may be multiplied by a coefficient corresponding to the light power ratio of the first and second laser beams. The optical system may be enclosed with a gas substantially having no absorption in the measured wavelength. This enhances the sensitivity in the identification of the impurity.

In this apparatus, the position of one of the first and second measuring means may be adjustable in order to equalize the first and second light path lengths, preventing divergence due to change of temperature or due to deterioration and making it possible to enhance reliability of the measurement.

BEST MODE FOR CARRYING OUT THE INVENTION

The best mode of the analysis method and apparatus for gases, according to an embodiment of the present invention, will be explained.

Figure 1:
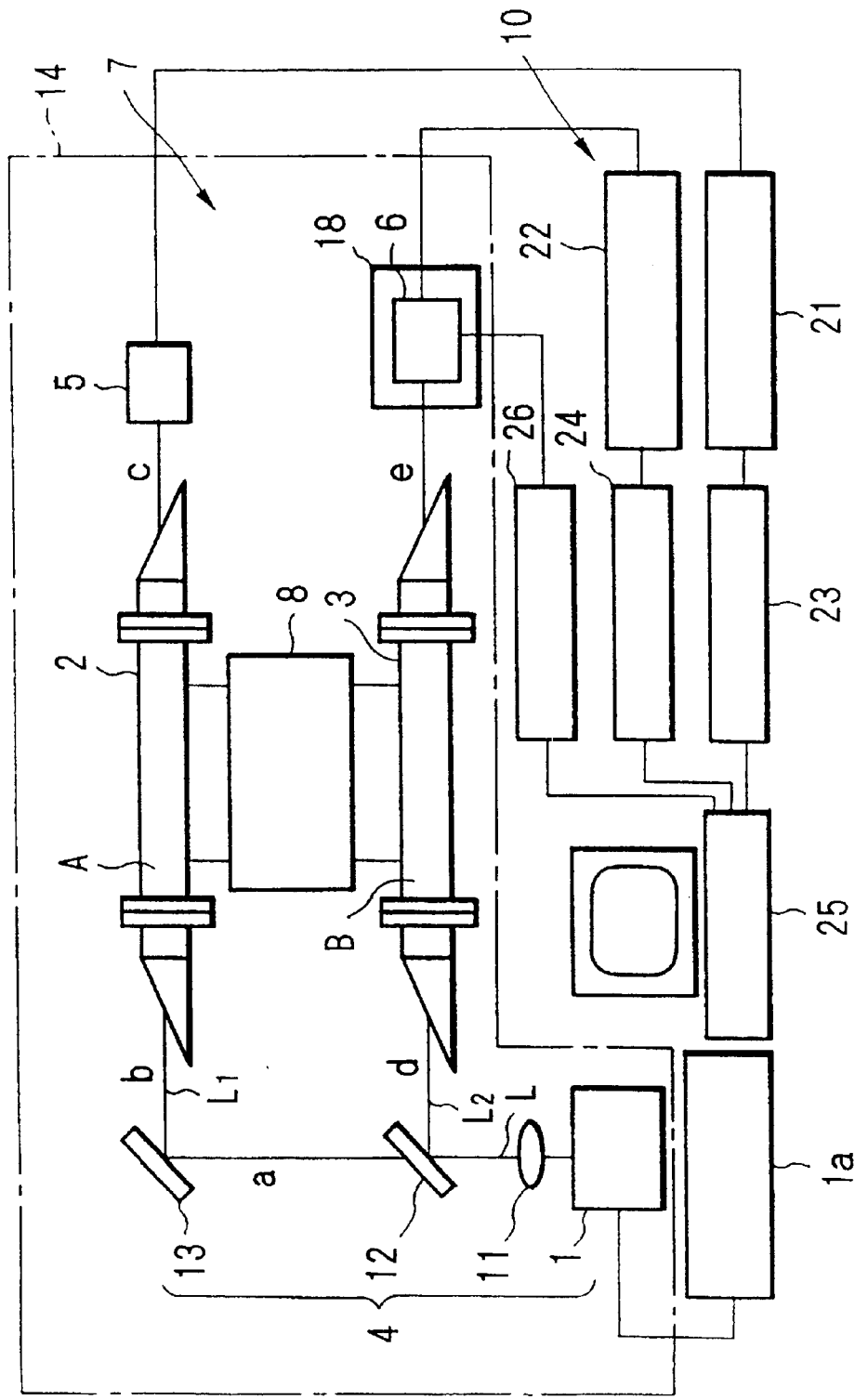
FIG. 1 is a schematic structural illustration showing a gas analysis apparatus of the present invention.

FIG. 1 shows an embodiment of a gas analysis apparatus according to the present invention. The gas analysis apparatus comprises a laser light source 1, a sample cell 2 for containing a gas A to be measured with a target impurity, a reference cell (cancel cell) 3 for containing a reference gas (cancel gas) B with no impurity, a light splitting means 4 for splitting the laser beam L from the light source 1 to pass a first laser beam L1 through the sample cell 2 and to pass a second laser beam L2 through the reference cell 3, a first detector 5 for measuring the intensity of the beam L1 passing through the sample cell 2, a second detector 6 for measuring the intensity of the beam L2 passing through the reference cell 3, a gas pressure equalizing supply means 8 for supplying the gases A and B into the cells 2 and 3 and for maintaining identical pressures in the cells 2 and 3, and a processor 10 for determining an absorption spectrum of the impurity in the gas A based on the difference measuring data from the first detector 5 and measuring data from the second detector 6.

A semiconductor laser capable of modulating a frequency is employed as the laser light source 1. The laser driver 1a supplies an injection current and a modulation signal to the semiconductor laser, and also controls the temperature of the laser element. Through this control, the oscillation frequency of the laser is varied so as to be near an absorption wavelength of the target impurity and is maintained at a constant value. Measurement of the absorption spectrum is carried out while varying the injection current to the laser to vary the frequency at regular intervals. The configuration of the driver 1a and the laser light source 1 is not limited to this embodiment, and, for example, a diode laser may be used.

The light splitting means 4 in an optical system 7 comprises a collimating lens 11 for collimating the frequency-modulated laser beam L from the laser light source 1, a half mirror 12 for splitting the beam L into first and second laser beams L1 and L2 at a light power ratio 1:1 by filtering out a part of the beam and reflecting the other part of the beam in a right-angled direction, and a mirror 13 for reflecting the first laser beam L1 in a right-angled direction to pass through the sample cell 2. The light splitting means 4 is not limited to this configuration, and for example, a waveguide-channel-type optical coupler and a optical fiber coupler (optical coupler) having superior transmission of the near infrared ray may be used.

The sample cell 2 and the reference cell 3 have identical shapes, materials, and dimensions, that is, identical optical characteristics. In the embodiment, the cells 2 and 3 are cylindrical with longitudinal lengths of more than 10 cm, internal diameters of approximately 20 mm, and the windows at both ends have angles of polarization. The first and second detectors 5 and 6 have light receiving elements capable of receiving the laser beam L with high sensitivity and identical light-receiving characteristics.

The optical system 7 which comprises the light source 1, the cells 2 and 3, the light splitting means 4, and the detectors 5 and 6, includes a gas which does not have much absorption at the wavelength region to be measured, such as nitrogen gas, and may be preferably accommodated in a purge means 14 for preventing atmospheric components such as moisture from leaking into the light paths. Specifically, the optical system 7 is enclosed in an outer case, which has a purge line for supplying a purge gas from a nitrogen purge gas cylinder and an exhaust line. With the purge means 14 enclosing the optical system 7, unnecessary absorption in light paths other than those in cells 2 and 3 can be prevented, and this improves the accuracy of measurement.

Figure 2:
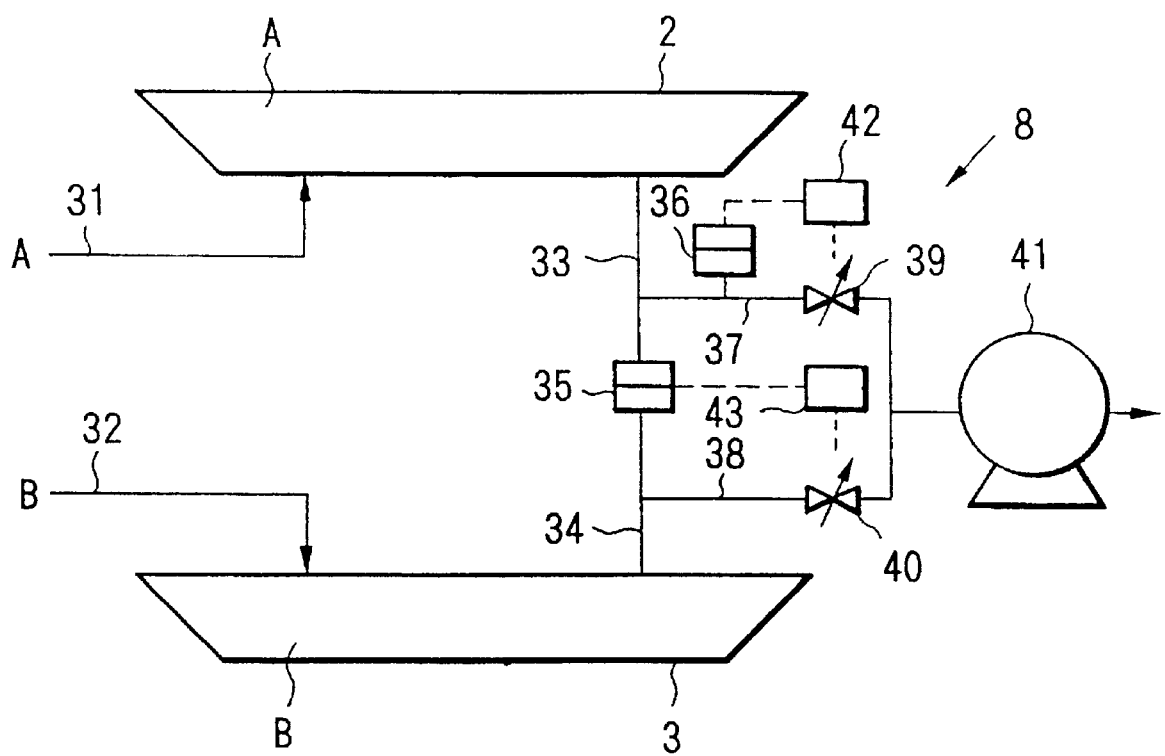
FIG. 2 is a schematic structural illustration showing a gas equalizing supply means of the present invention.
Figure 3:
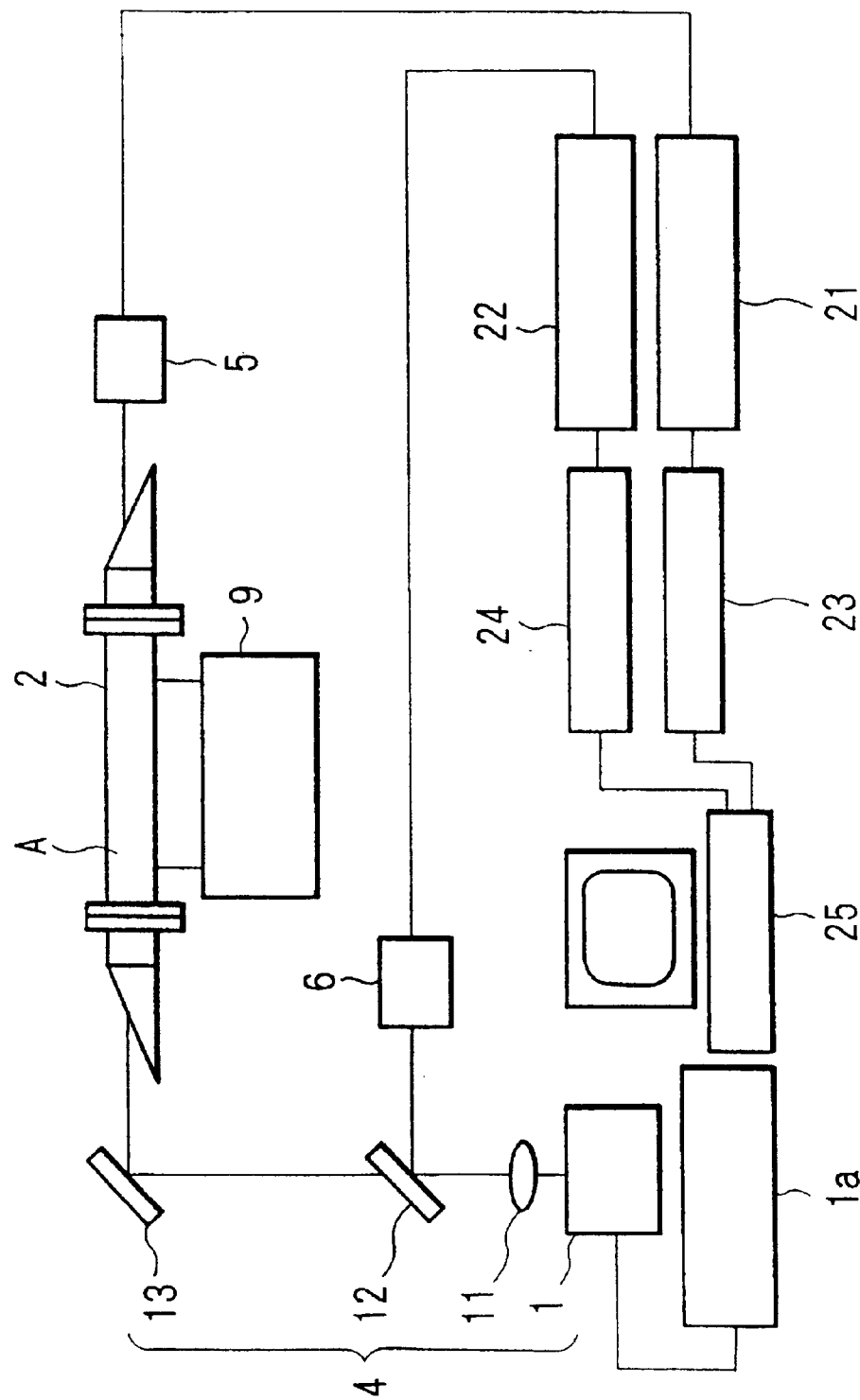
FIG. 3. is a schematic structural illustration showing a gas analysis apparatus of the prior art.
Figure 4:
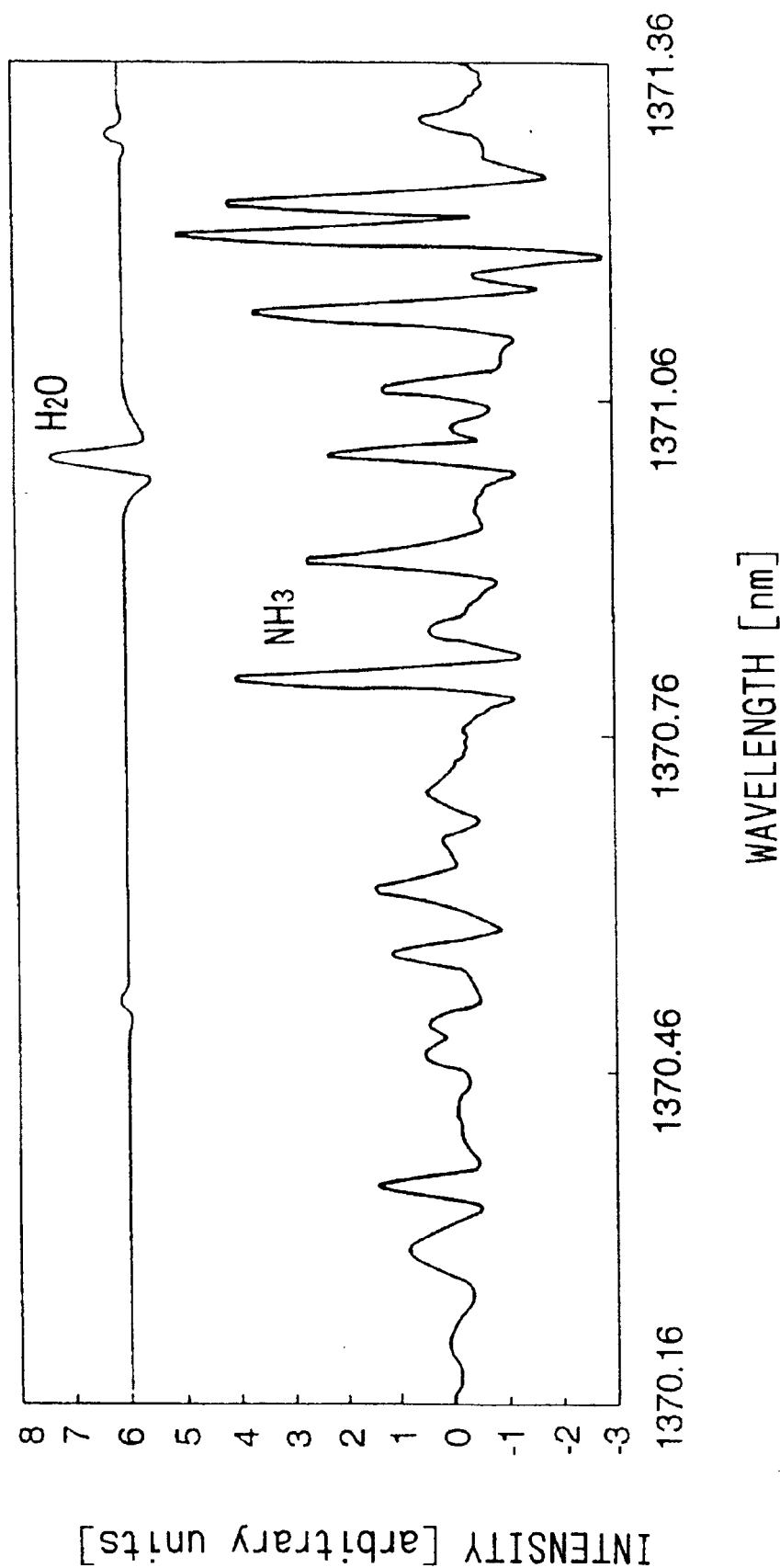
FIG. 4 is a graph showing absorption spectra of $NH_3$ and $H_2O$ measured by the gas analysis apparatus of the prior art.
Figure 5:
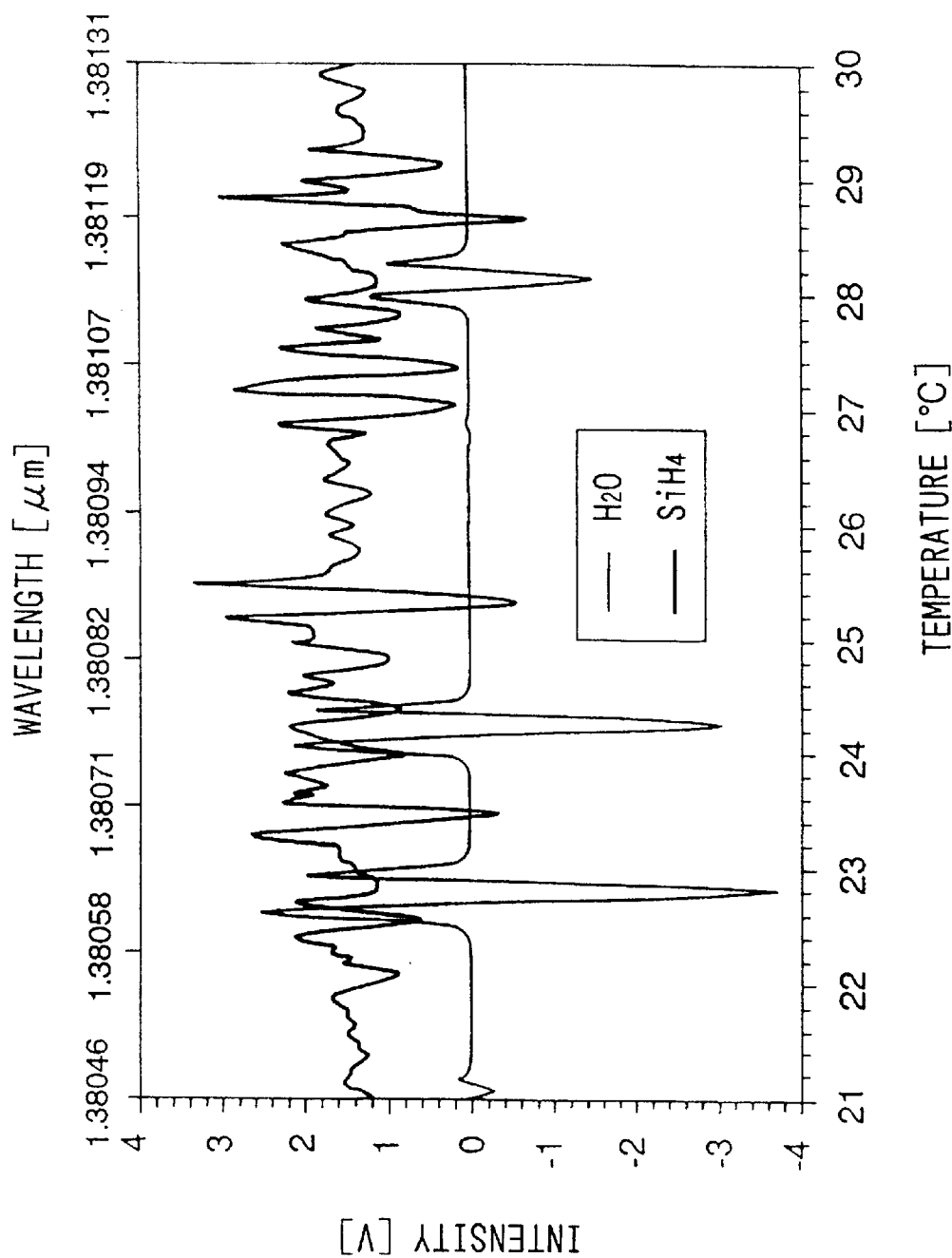
FIG. 5 is a graph showing absorption spectra of $SiH_4$ and $H_2O$ measured by the gas analysis apparatus of the prior art.
Figure 6:
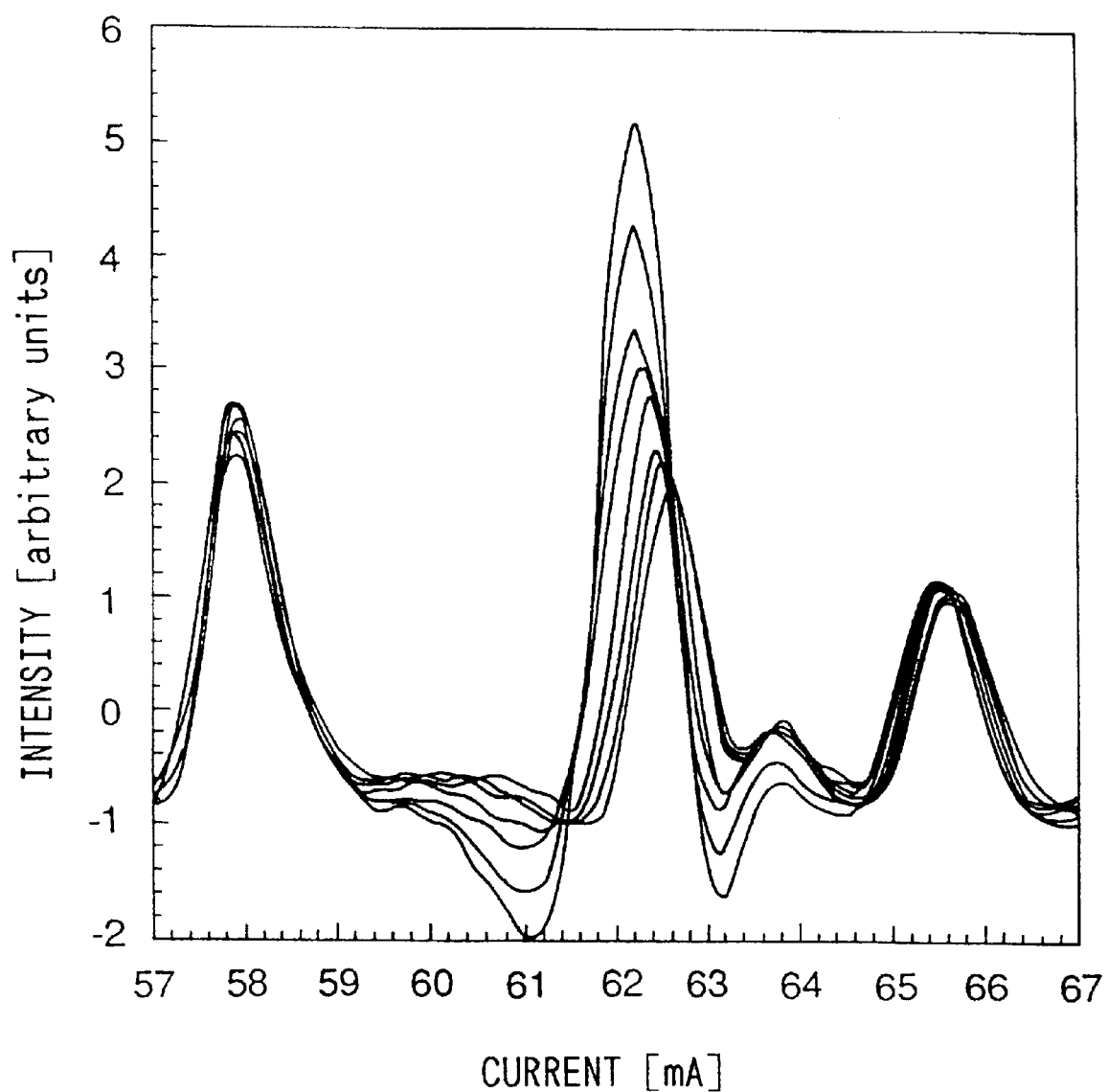
FIG. 6 is a graph showing spectra obtained by the measurement in the case where $H_2O$ is added to the $NH_3$ gas of the prior art.
Figure 7:
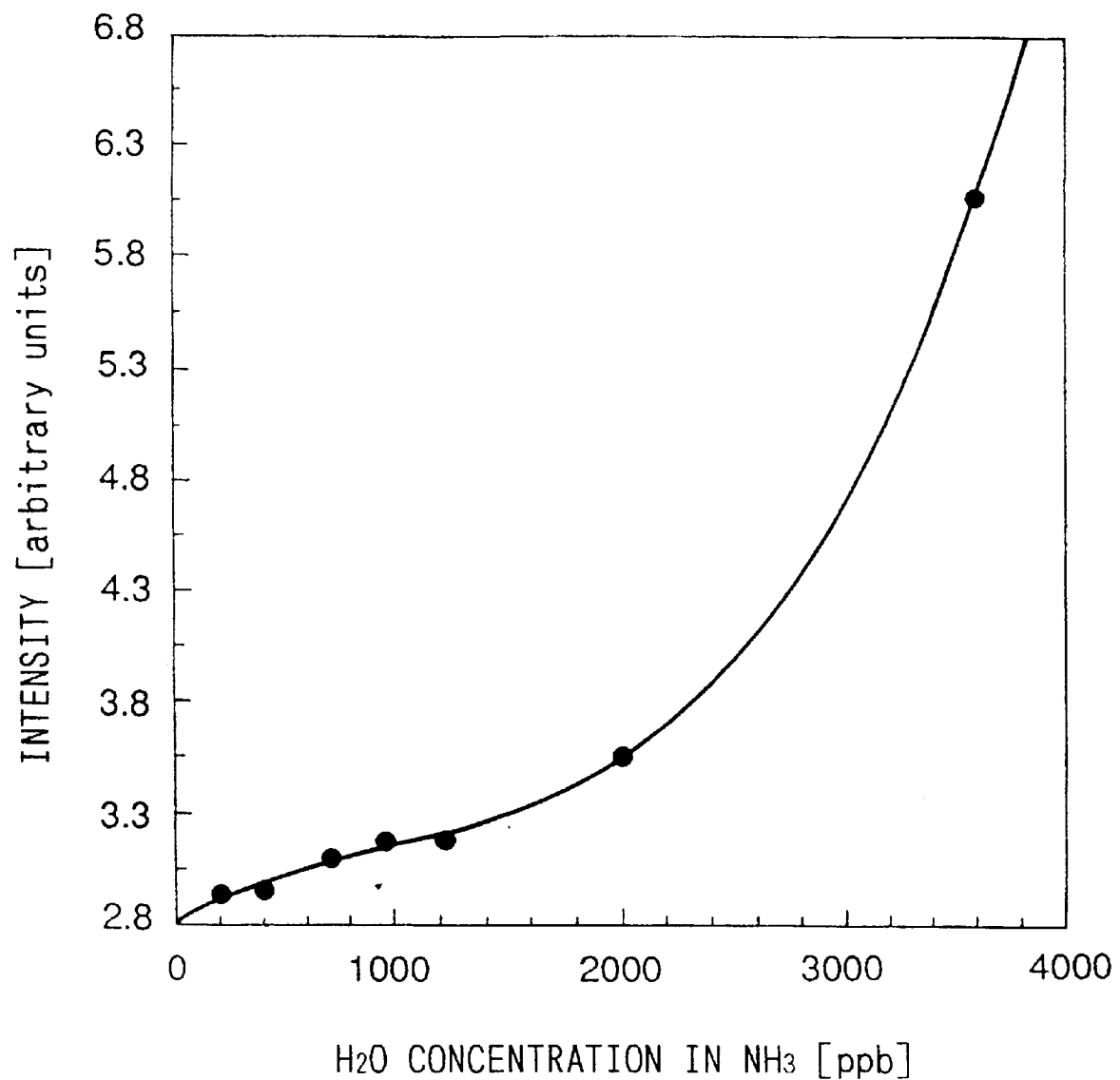
FIG. 7 is a graph showing a calibration curve obtained from the result of the measurement of FIG. 6.

As shown in FIG. 2, the gas pressure equalizing supply means 8 comprises a sample gas line 31 for introducing the gas A to be measured into the sample cell 2, a reference gas line 32 for introducing the reference gas B into the reference cell 3, sample and reference gas exhaust lines 33 and 34 for exhausting the gases from the sample cell 2 and from the reference cell 3, a differential pressure gauge 35 connected to the exhaust gas lines 33 and 34, a pressure gauge 36 in the exhaust lines of the sample cell, control valves 39 and 40 in both exhaust gas lines 37 and 38, and a exhaust pump 41 in the lower course of the control valves 39 and 40. A processor 42 adjusts opening of the control valve 39 is adjusted so that the pressure measured by the pressure gauge 36 in the sample gas exhaust lines 33 and 37 is set to a predetermined value. A processor 43 adjusts opening of the control valve 40 so that the pressure (differential pressure) measured by the differential pressure gauge 35 is set to zero.

With the gas pressure equalizing supply means 8, the differential pressure between the sample cell 2 and the reference cell 3 is measured, and the pressures in the cells 2 and 3 are equalized by adjusting the opening of the control valve 40 of the reference part.

As shown in FIG. 1, the processor 10 comprises a first lock-in amplifier 21 for amplifying the output from the first detector 5, a second lock-in amplifier 22 for amplifying the output from the second detector 6, a first AD converter 23 for converting the output from the second lock-in amplifier 21 into a digital signal, and a second AD converter 24 for converting the output from the second lock-in amplifier 22 into a digital signal. A computer 25 receives the output signals from the first and second AD converters 23 and 24 and from a D/A converter 26, determines an absorption spectrum of an impurity in the gas by subtracting the measuring data of the second detector 6 from the measuring data of the first detector 5, and displays the result of the calculation.

The processor 10 converts the outputs form the first and second detector into digital signals in every measured wavelength region, multiplies the measuring data from the second detector 6 by a coefficient corresponding to the ratio of the light powers of the first and second laser beams, and subtracts the measuring data from the second detector 6 from the measuring data of the first detector 5 to determine the absorption spectrum of the gas A to be measured. The calculation result of the processor 25 is displayed on a display, and a chart of the absorption spectrum is stored in a storage medium.

A first light path from the light splitting point of the half mirror 12 via the sample cell 2 to the first detector 5 is set to be equal to a second light path from the half mirror 12 via the reference cell 3 to the second detector 6. The first light path length is the total of the light path "a" from the half mirror 12 to the mirror 13, the light path "b" from the mirror 13 to an entrance window of the sample cell 2, the light path "c" from an exit window of the sample cell 2 to the first detector 5, and the length of the sample cell 2. The second light path length is the total of the light path "d" from the half mirror 12 to an entrance window of the reference cell 3, the light path "e" from an exit window of the reference cell 3 to the second detector 6, and the length of the reference cell 3. Since the lengths of the cells are identical, as the first light path length a+b+c is compared with the second light path length d+e except the lengths of the cells 2 and 3, when the cells 2 and 3 and the detectors 5 and 6 are relatively positioned so that b+c is equal to d+e, the first light path is longer than the second light path by the length "a" from the half mirror 12 to the mirror 13. Accordingly, at least one of the light paths "d" and "e" may be set to be greater than one of the light paths "b" and "c", thereby making both light paths identical.

The second detector 6 is attached to an X-Y stage 18 for making the first light path length equal to the second light path length. The light path "e" can be changed by fine adjustment of the position of the second detector 6. Preferably, the adjustment of the second detector 6 may be controlled by the computer 25 which provides an output signal through the D/A converter 26 to the X-Y stage 18.

The gas analysis method using the above apparatus of the present invention will be explained. The gas A to be measured has a main component of $NH_3$ or $SiH_4$ having interference absorption at the wavelength region scanned in identification for the target impurity such as $H_2O$. The absorption spectra of an impurity such as $H_2O$ cannot be accurately measured with the conventional method because of the interference absorption of $NH_3$ or $SiH_4$. The gas A to be measured is not limited to the above gases but may be nitrogen, oxygen, argon, or other gases used in the manufacturing of semiconductor materials.

The frequency-modulated laser beam L is emitted from the semiconductor laser 1, is collimated by the lens 11, and is split by the half mirror 12 into the first and second laser beams L1 and L2 at the light power ratio 1:1. The first laser beam L1 is reflected on the mirror 13, enters the sample cell 2, passes through the gas A in the cell 2, and enters the first detector 5. The second laser beam L2 passes the reference cell 3 which includes the gas with no impurity (gas consisting of the main component of the gas A), and enters the second detector 6. The beams L1 and L2 entering the first and second detector 5 and 6 are converted into electrical signals, which are supplied to the lock-in amplifiers 21 and 22.

Reference signals for the lock-in amplifier 21 and 22 are identical with or a double wave of modulation signals of the semiconductor laser. The output signals from the lock-in amplifiers 21 and 22 are converted by the AD converters 23 and 24 into digital signals, which are stored in the computer 25.

The laser driver 1a provides an injection current and a modulation signal to the semiconductor laser, and controls the temperature of the laser element. When the target impurity is an atmospheric component, the optical system should be covered with the purge box which contains nitrogen.

The wavelength of the laser is varied so as to be near the center of the absorption wavelength of the target impurity by controlling the temperature of the laser element, which is maintained at a constant value. The absorption spectrum is measured while the wavelength of the semiconductor laser is being scanned at regular intervals by varying the injection current. The measuring data from the sample channel and the cancel channel are simultaneously outputted from the two AD converters in every step. The pressures and amounts of flow inside the sample cell 2 and the reference cell 3 are controlled to be identical.

With the gas analysis apparatus, the laser beam L is split into the first and second laser beams L1 and L2, the intensity of the first laser beam L1 passing through the sample cell 2 including the gas A with the target impurity is measured, the intensity of the second laser beam L2 passing through the reference cell 3 including the reference gas B with no impurity is measured, and the absorption spectrum of the target impurity is determined by subtracting the measuring data of the second light path from the measuring data of the first light path. The absorption of the impurity can be measured with high accuracy based on the difference between the absorption in the sample cell 2 (the absorption of the impurity and the absorption of the matrix gas) and the absorption in the reference cell 3 (the absorption of the matrix gas). Accordingly, impurities in a gas such as $NH_3$ or $SiH_4$ having the interference absorption can be identified with high sensitivity and accuracy.

The first and second light paths may preferably have identical optical characteristics and the pressures and the flow rates in the sample cell and the reference cell may be equalized, so that the background absorption in the both light paths becomes identical and the difference between the absorption of the sample cell 2 and the absorption of the reference cell 3 coincides with the absorption of the impurity, thereby enhancing the sensitivity in the identification of the impurity.

The outputs from the first and second light paths may be simultaneously converted into digital signals at every measured wavelength region, the measuring data from the second light path may be multiplied by a coefficient corresponding to the light power ratio of the first and second laser beams, and the measuring data from the second detector 6 is subtracted from the measuring data of the first detector 5, so that the absorption spectrum of the target impurity is accurately measured and the trace impurity can be identified.

The laser beams passing from the light source 1 to the detectors 5 and 6 are prevented from being attenuated due to the moisture, etc., in the air because the optical system 7 is enclosed in the gas substantially having no absorption in the measured wavelength. The measurement of an impurity of a component such as moisture in the air can be therefore carried out with high sensitivity.

The attenuation and luminous intensities of the laser beams L1 and L2 passing from the light source 1 to detectors 5 and 6 are equalized by setting the first light path length to be equal to the second light path length, thereby improving detection sensitivity.

Further, the difference between the first and second light path lengths because of a change in temperature or due to deterioration of the optical system can be prevented by adjusting the position of one of the second detector and the first detector, making it possible to enhance reliability of the measurement. The reference cell or the sample cell may be movable with the second detector or the first detector.

Furthermore, the pressures in the sample cell and the reference cell are equalized by the gas pressure equalizing supply means 8, so that measurement can be carried out with high accuracy even when the pressure of the matrix gas is varied.

(Embodiment 1)

Trace moisture in ammonia is measured using an apparatus constructed as shown in FIG. 1. The semiconductor laser 1 of the light source is a DFB laser having a band of 1.37 $\mu$m. Frequency modulation is carried out by adding a sine wave of 4 kHz to the injection current for the laser. The sample cell 2 and the reference cell 3 are made of stainless steel, and have a light path of 90 cm and windows with angles of polarization. $NH_3$ containing an $H_2O$ impurity is constantly introduced into the sample cell 2 at a pressure of 50 Torr at a flow velocity of 400 sccm. $NH_3$ with no impurity is introduced into the reference cell 3 at a pressure of 50 Torr.

The first and second detectors 5 and 6 are Ge photo diodes having identical model numbers. The lock-in amplifiers 21 and 22 and the AD converter 23 and 24 in both lines have identical model numbers.

The half mirror 12 is used to split the light beam, and since the split light power ratio is actually 1:1.15, the cancel coefficient is set to 1.2.

Figure 8:
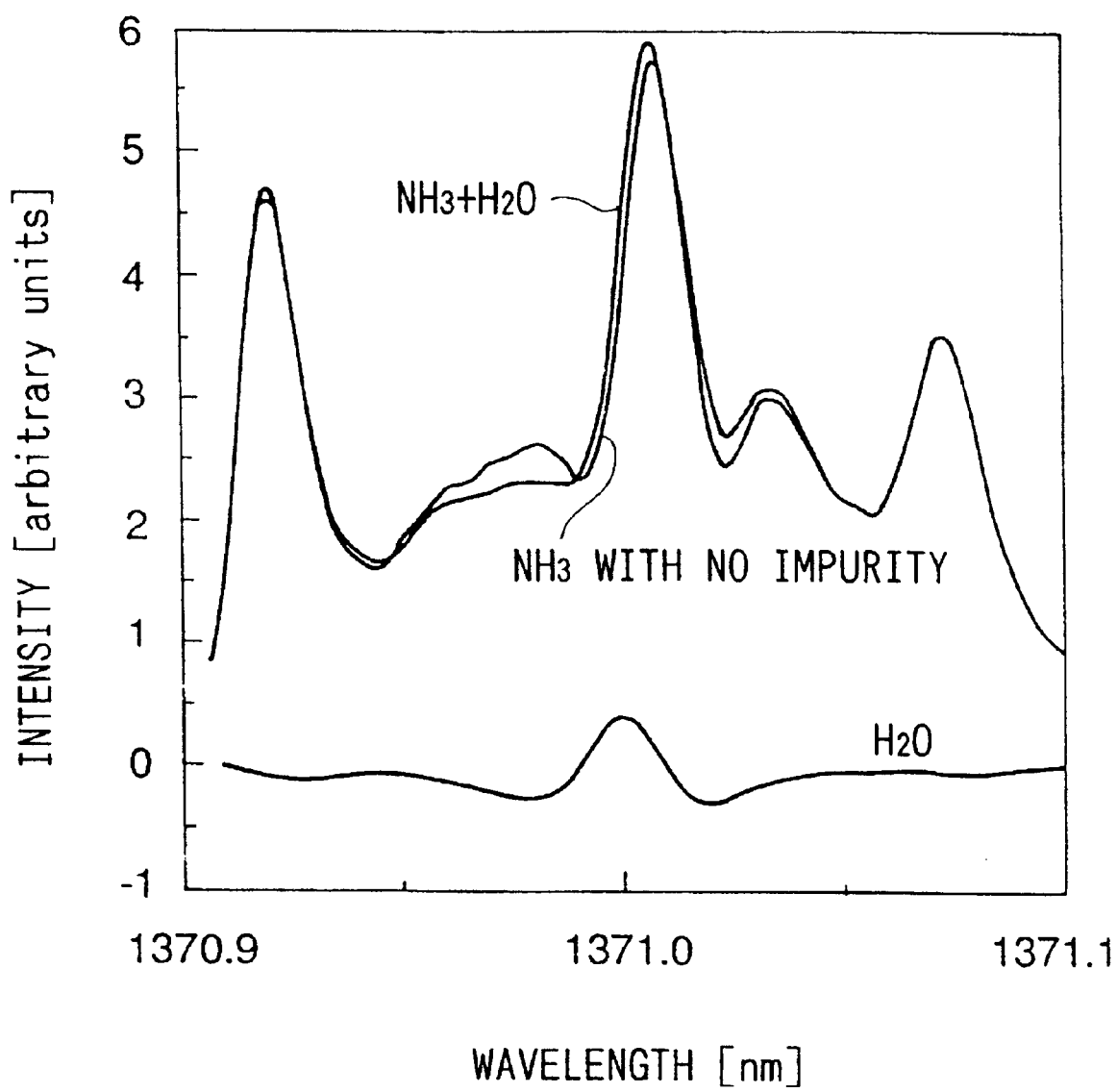
FIG. 8 is a graph showing absorption spectra of $NH_3$ and $H_2O$ measured by the gas analysis apparatus of the present invention.
Figure 9:
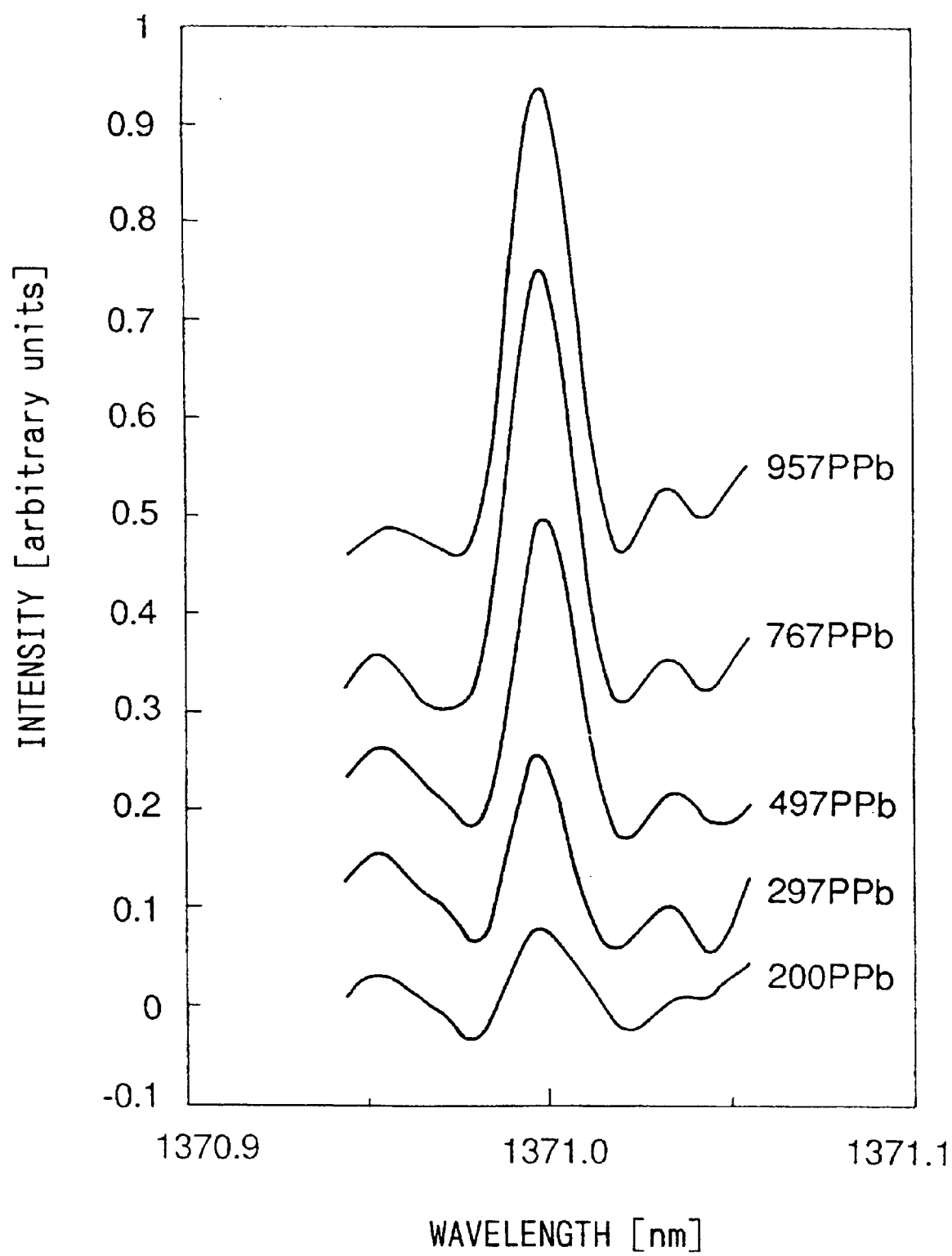
FIG. 9 is a graph showing spectra when $H_2O$ in $NH_3$ is varied, measured by the gas analysis apparatus of the present invention.
Figure 10:
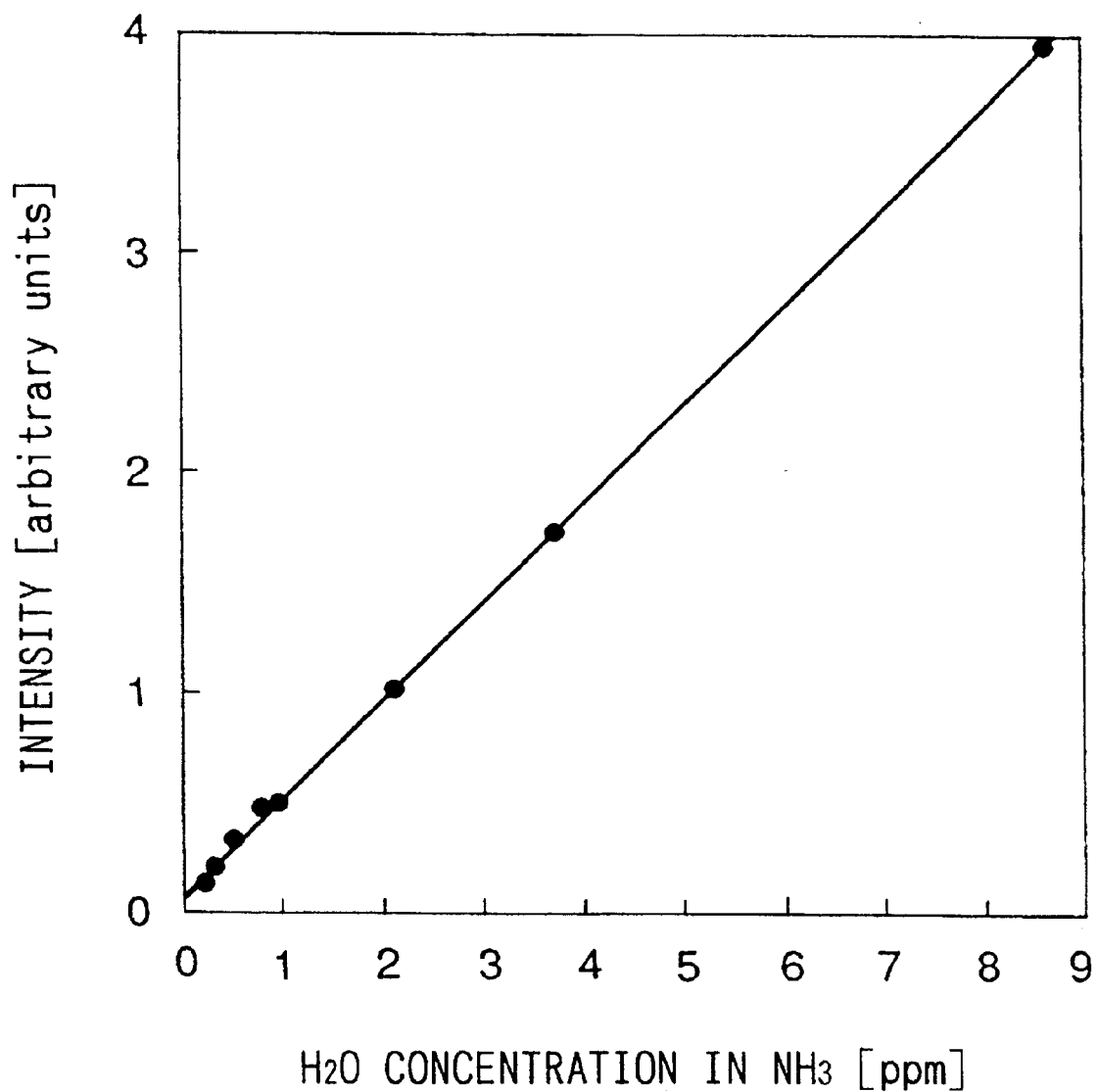
FIG. 10 is a graph showing a calibration line obtained from the result of the measurement of FIG. 9.

FIG. 8 shows measuring results of the sample cell 2 and of reference cell 3, and a calculation result obtained from subtraction of the interference absorption of $NH_3$, the moisture existing in the purge box, and the noise from the light source. FIG. 9 shows spectra in the case where the moisture concentration is varied under the same measurement conditions as FIG. 8. FIG. 10 shows a calibration line, which indicates good linearity.

(Embodiment 2)

The gas analysis apparatus with the gas pressure equalizing supply means 8 shown in FIG. 2 is used. The gas A to be measured is introduced into the sample cell 2 through the sample line 31, and is exhausted through the pressure gauge 36 and the control valve 39 from the exhaust pump 41. The pressure gauge 36 is a diaphragm absolute pressure gauge, which measures the pressure in the sample cell 2. The full range of the pressure gauge 36 is 0 to 100 Torr, and the resolution is 0.5 Torr. A pressure signal from the pressure gauge 36 is supplied to the processor 42, and is compared with a predetermined signal. The signal obtained from the comparison is used as a feedback signal for controlling the opening of the control valve 39. The opening of the control valve 39 is controllable using a piezo-element.

The reference gas B is introduced into the reference cell 3 through the cancel line 32 while the amount of flow is controlled, and is exhausted through the control valve 40 from the exhaust pump 41. The differential pressure gauge 35 is a diaphragm differential pressure gauge, which equalizes the pressures of the sample cell 2 and the reference cell 3. The full range of the differential pressure gauge is 0 to 100 Torr, and the resolution is 0.01 Torr. A pressure signal from the differential pressure gauge 35 is supplied to the processor 43, which controls the opening of the control valve 40 so as to set the difference between the pressure to zero. The reference gas B is not necessarily vented, and may be contained by a valve (not shown) at the entrance for the reference gas and by a valve (not shown) between the differential pressure gauge 35 and the exhaust pump 41.

Figure 11:
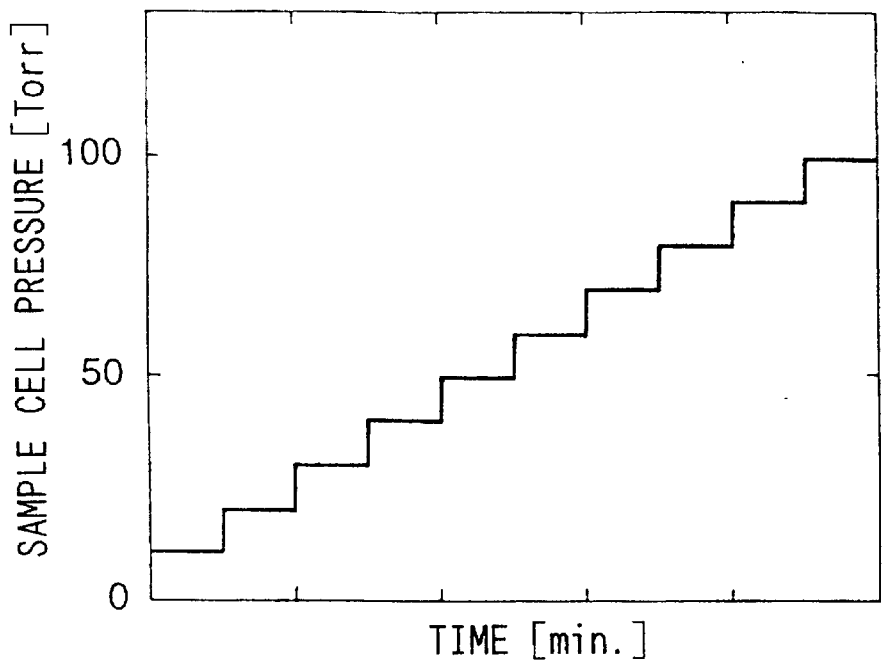
FIG. 11 is a graph showing a pressure in a sample cell (first cell) when a setting pressure is varied, measured by the gas analysis apparatus of the present invention.
Figure 12:
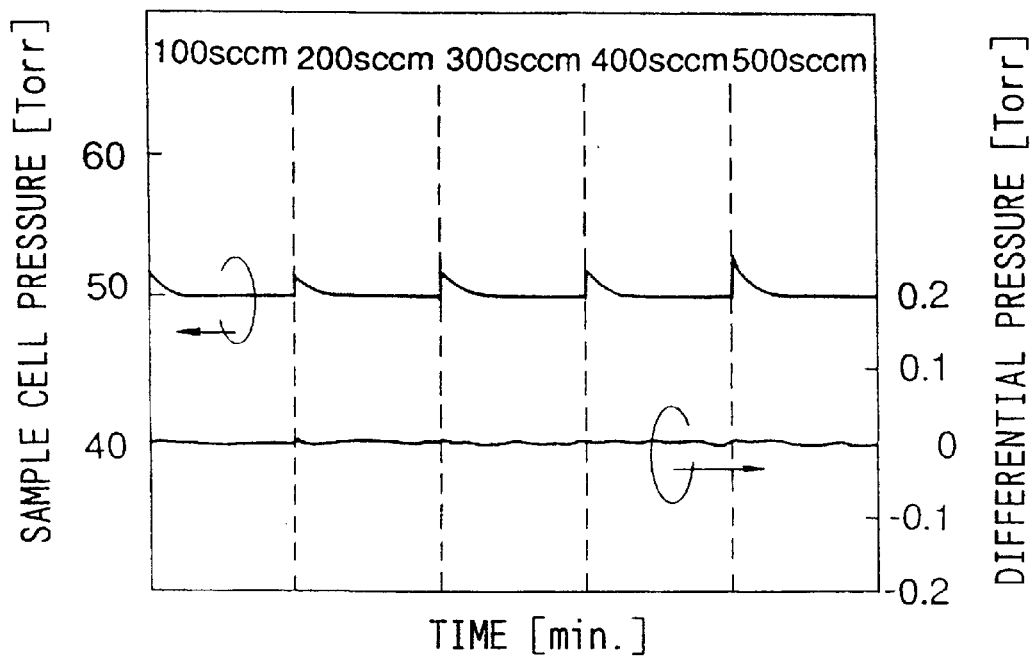
FIG. 12 is a graph showing a pressure in the sample cell when the amount of flow of the sample gas is varied and a differential pressure between the sample cell and a reference cell (second cell) when the amount of flow of the reference gas is varied, in the gas analysis apparatus of the present invention.

Measurement for pressure controllability in the sample cell 2 is carried out, and FIG. 11 shows the result. When the amount of flow of the sample gas is set to 200 cc/min. and the pressure is increased from 10 to 100 Torr in 10 Torr increments, the differences between measuring values and setting values are within ±1 Torr at every measuring stage. When the pressure is set to 50 Torr and the amount of flow of the sample gas is varied from 100 to 500 cc/mmn. by 100 cc/min., the measuring values are 50 ±1 Torr at any measuring step (as shown in FIG. 12). FIG. 12 also shows the controllability of the differential pressure between the sample cell 2 and the reference cell 3. When the amount of flow of the reference gas is varied from 100 to 500 cc/min. in 100 cc/min. increments, the differential pressures are less than 0.01 Torr at every stage.

With the gas pressure equalizing supply means, the pressure in the sample cell 2 can be adjusted properly and accurately, and the pressures in the sample cell 2 and the reference cell 3 can be equalized. Back flow can be prevented because there is no differential pressure between the sample cell 2 and the reference cell 3, and accordingly, an optional exhaust system is not necessary. The apparatus requires only one exhaust pump and can be reduced in size.

(Embodiment 3)

Figure 13:
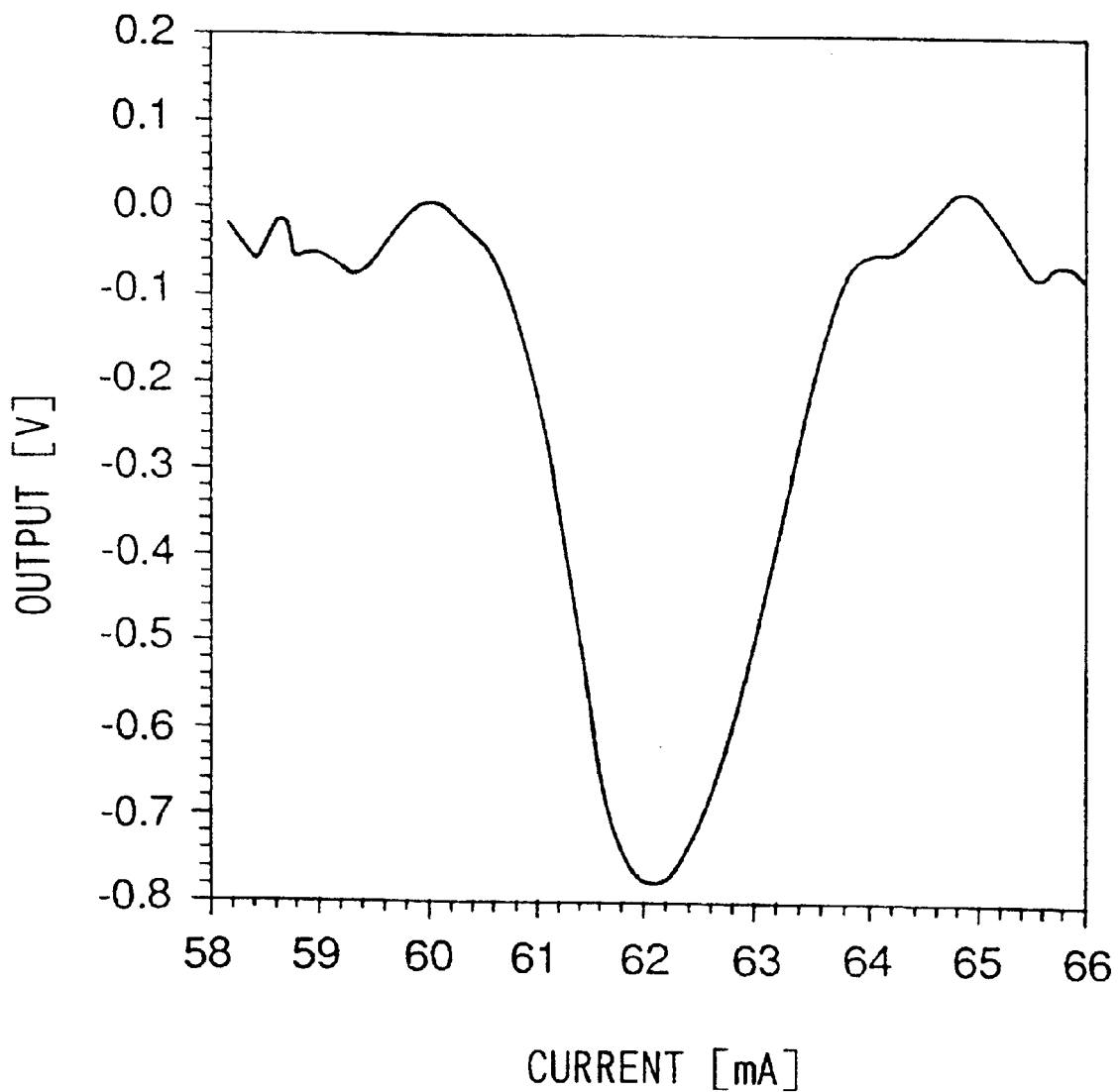
FIG. 13 is a graph showing an absorption spectrum of moisture in the light path other than in the cells when moisture concentration in the sample cell is zero, measured by the gas analysis apparatus of the present invention.

With the gas analysis apparatus shown in FIG. 1, the adjustment of the light path lengths is carried out. $N_2$ containing moisture is introduced into the sample cell 2, where the pressure is set to 50 Torr and the amount of flow is set to 300 cc/min. $N_2$ with no impurity is enclosed in the reference cell at a pressure of 760 Torr. FIG. 13 shows a measured spectrum when the moisture concentration in the sample cell is 0 ppb. The differential spectrum indicates a sharp drop because of moisture existing in the light paths other than in the cells. The absorption line is greatly decreased from a base line in a negative direction around the center of the measured wavelength. This is because the influence due to the moisture existing in the second light path from the half mirror 12 to the second detector 6 other than the reference cell 2 is greater than the influence due to the moisture in the first light path other than the sample cell 3.

Figure 14:
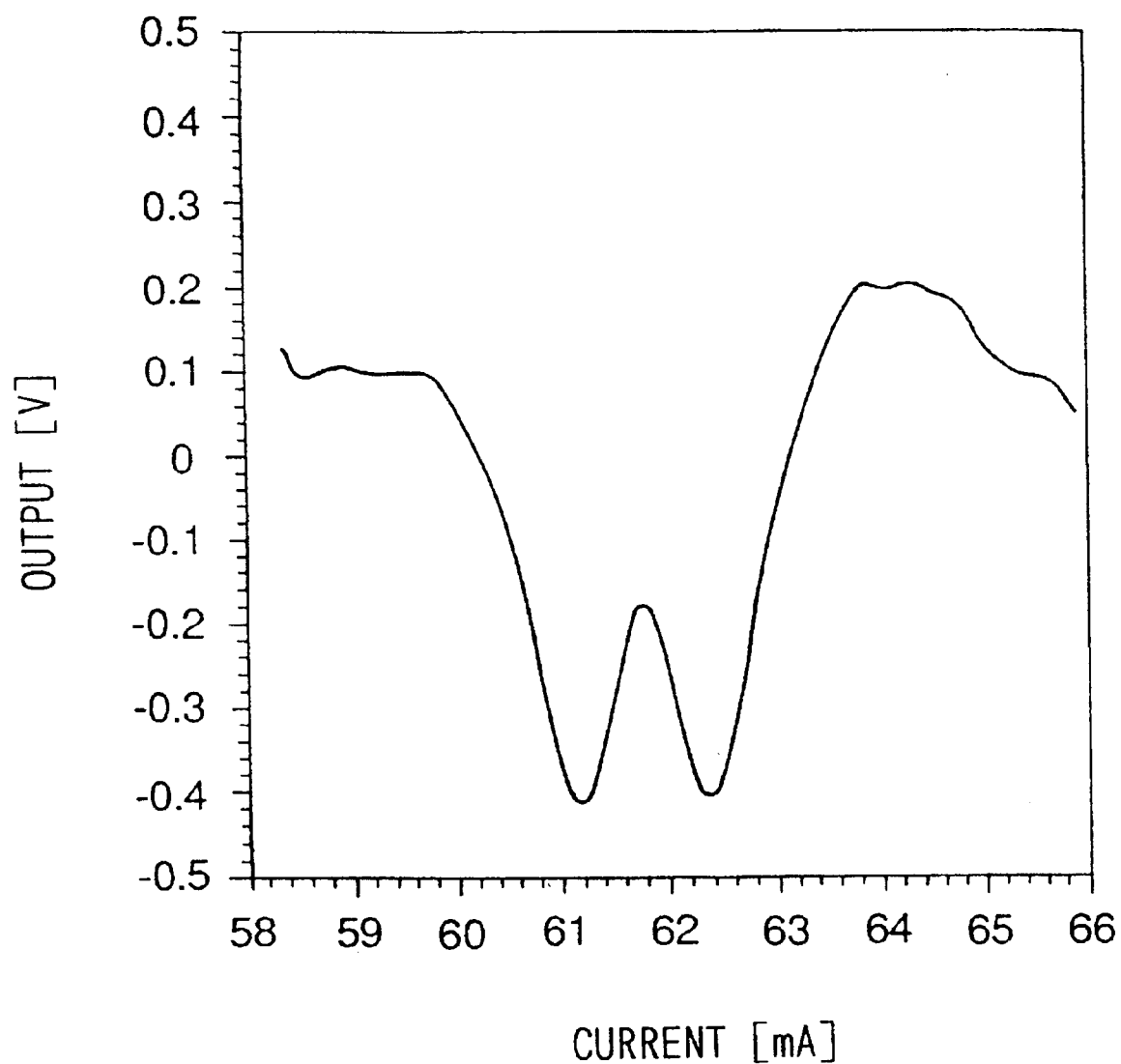
FIG. 14 is a graph showing an absorption spectrum of moisture in the light path other than in the cells when moisture concentration in the sample cell is 28 ppb, measured by the gas analysis apparatus of the present invention.

FIG. 14 shows a measured spectrum when the moisture concentration in the sample cell is 28 ppb. A sharp rising portion of an absorption in the sample cell 2 overlaps the sharp dropping portion from the base line.

When the light path lengths are not properly adjusted, the shape of the measured absorption spectrum is changed because of the trace moisture existing in the light paths other than in the cells. This leads to some difficulties in the measurement when the wavelength of the laser is set to the center of the absorption line.

An automatic adjustment mechanism is provided to minimize the influence on the beam. Specifically, the second detector 6 is attached on an electrically driven stage 18 (X-Y stage) movable along X- and Y-axes. The X-axis is parallel to the beam axis while the Y-axis is perpendicular to the X-axis. The X-Y stage 18 is connected through two D/A converters to a computer 25, which can controls the movement along the X- and Y-axis. The adjustment is carried out, based on a parameter which is a difference (A–B) between two measuring values at the center of the absorption wavelength at one point (A) and at another point (B) apart from the point (A) by more than 0.1 $cm^{-1}$.

The adjustment is made as follows:

(a) the pressure in the cell is adjusted, (b) the baseline is adjusted, and (c) the cancel coefficient is optimized.

In the steps (a) and (b), the Y-axis is first adjusted because of the great signal variation along the Y-axis (rough adjustment). The rough adjustment is repeated so as to minimize the A–B value, and fine adjustment along the X-axis is made.

Figure 15:
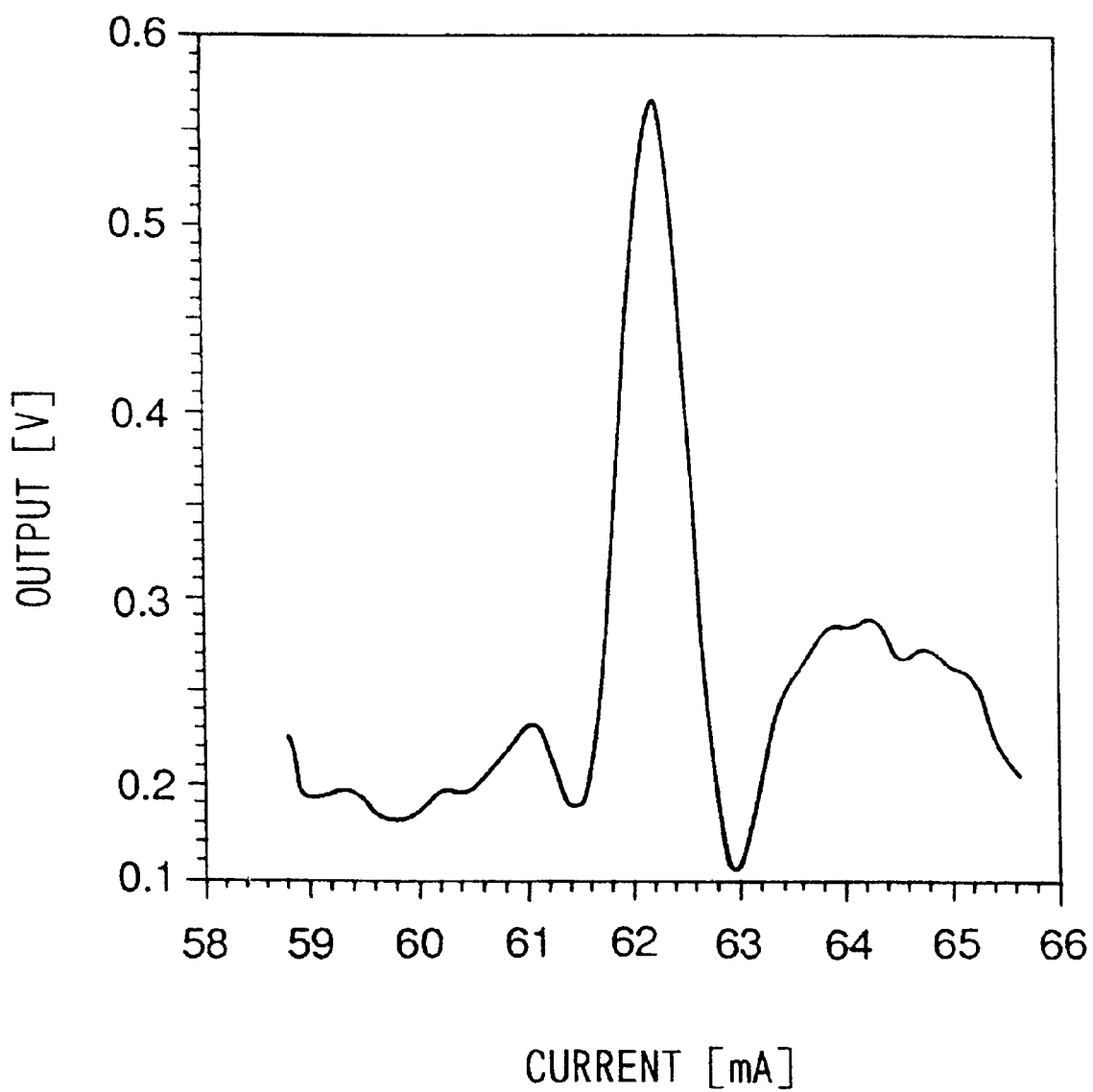
FIG. 15 is a graph showing an absorption spectrum after the light path lengths are adjusted and optimization of a coefficient is made, in the gas analysis apparatus of the present invention.
Figure 16:
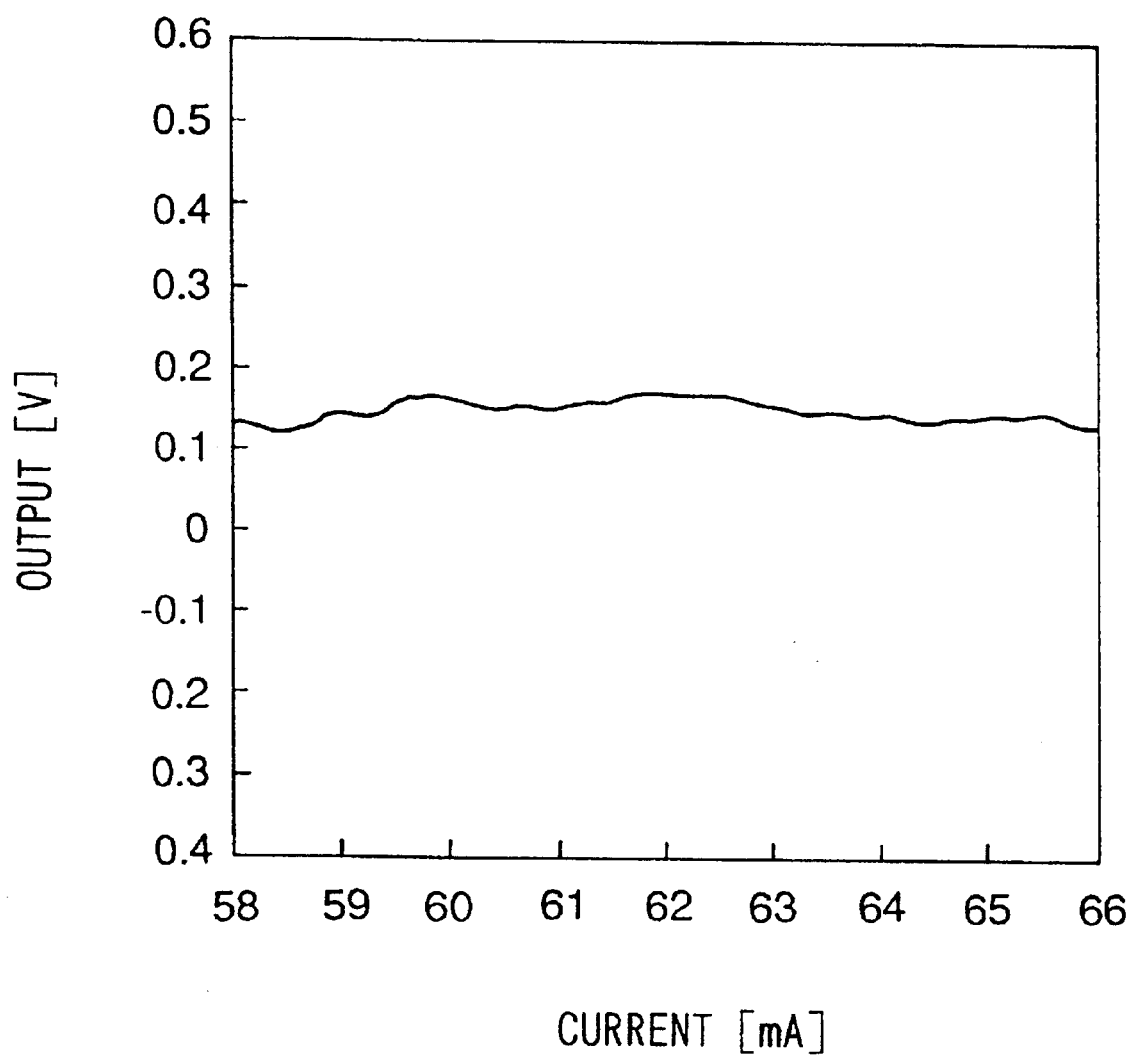
FIG. 16 is a graph showing a differential spectrum after the light path lengths are adjusted when moisture concentration in the sample cell is zero, in the gas analysis apparatus of the present invention.

In step (c), the cancel coefficient requires optimization because the light power ratio for the two detectors has been varied by the adjustment. Measuring data, for example, at eleven points, are averaged, and difference values between average data and measured data are obtained. The cancel coefficient is determined by investigating the value which best fits to minimizes the distribution (or the standard deviation) of the difference values, while varying from –0.5 to +0.5 with respect to the original value by 0.01. FIG. 15 shows measuring data after the adjustment of the light path length. FIG. 16 shows the differential spectrum when the moisture concentration in the sample cell is 0 ppb and the light paths are equalized.

This invention may be embodied in other forms or carried out in other ways without departing from the spirit thereof. The present embodiments are therefore to be considered in all respects illustrative and not limiting, the scope of the invention being indicated by the appended claims, and all modifications falling within the meaning and range of equivalency are intended to be embraced therein.

We claim:

1. A method for analyzing an impurity in a gas, comprising the steps of introducing a gas with an impurity into a first cell;

introducing a gas with no impurity into a second cell;

maintaining identical pressures in said first and second cells;

irradiating a light from a light irradiating source;

varying the frequency of said light over a frequency spectrum including an absorption frequency of said impurity;

splitting the light into a first beam and a second beam with a splitting device passing said first beam through said first cell;

passing said second beam through said second cell;

measuring an intensity of light passed through said first cell over said frequency spectrum with a first measuring device;

measuring an intensity of light passed through said second cell over said frequency spectrum with a second measuring device; and determining an absorption spectrum of the impurity in the gas with the impurity based on a difference between from measured with said first measuring device and data measured with said second measuring device.

2. A method for analyzing an impurity in a gas, according to claim 1, further comprising the step of adjusting a first light path from said splitting device via said first cell to said first measuring device and a second light path from said splitting device via said second cell to said second measuring device to have identical optical characteristics.

3. A method for analyzing an impurity in a gas, according to claim 1, further comprising the step of setting a length of a first light path from said splitting device via said first cell to said first measuring device to be equal to a length of a second light path from said splitting device via said second cell to said second measuring device.

4. A method for analyzing an impurity in a gas, according to claim 3, further comprising the step of adjusting the lengths of said first and second light paths by shifting one of said first and second measuring devices.

5. A method for analyzing an impurity in a gas, according to claim 1, wherein introducing said gases into said first and second cells is performed at identical flow rates.

6. A method for analyzing an impurity in a gas, according to claim 1, further comprising the step of converting the data measured with said first and second measuring devices into digital signals.

7. A method for analyzing an impurity in a gas, according to claim 1, further comprising the step of multiplying one of the data measured with said first and second measuring devices by a coefficient corresponding to a ratio of light powers of said first and second beams.

8. A method for analyzing an impurity in a gas, according to claim 7 further comprising the step of adjusting lengths of said first and second light paths by shifting one of said first and second measuring devices; and determining said coefficient based on the ratio of the light powers of said first and second beams after shifting said one of said measuring devices.

9. A method for analyzing an impurity in a gas, according to claim 1, further comprising the step of covering light paths from said light irradiating source to said first and second measuring devices with a purge device comprising a gas having no optical absorption in a range of wavelength to be measured.

10. A method for analyzing an impurity in a gas, according to claim 1, wherein varying the frequency of said light comprises varying an injection current of a laser.

11. A method for analyzing an impurity in a gas, according to claim 1, wherein:

introducing said gas with said impurity into said first cell comprises introducing a matrix gas and an impurity; and introducing said gas with no impurity into said second cell comprises introducing said matrix gas.

12. An analysis apparatus for analyzing an impurity in a gas, comprising:

a light irradiating source;

a first cell configured to contain a gas with an impurity to be measured;

a second cell configured to contain a gas with no impurity;

a frequency varying device configured to vary the frequency of a light irradiated from said light irradiating source over a frequency spectrum including an absorption frequency of said impurity;

a splitting device configured to split the light from said light irradiating source in order to pass a first beam through said first cell and to pass a second beam through said second cell;

a first measuring device configured to measure the intensity of said first beam passing through said first cell over said frequency spectrum;

a second measuring device configured to measure the intensity of said second beam passing through said second cell over said frequency spectrum;

a gas supply mechanism configured to supply the gas with the impurity to said first cell and the gas with no impurity into said second cell while maintaining identical pressures in said first and second cells; and a determination mechanism configured to determine an absorption spectrum of the impurity in the gas with the impurity based on a difference between data measured with said first measuring device and data measured with said second measuring device.

13. An analysis apparatus for analyzing an impurity in a gas, according to claim 12, wherein a first light path from said splitting device via said first cell to said first measuring device and a second light path from said splitting device via said second cell to said second measuring device have identical optical characteristics.

14. An analysis apparatus for analyzing an impurity in a gas, according to claim 12, wherein a length of a first light path from said splitting device via said first cell to said first measuring device is equal to a length of a second light path from said splitting device via said second cell to said second measuring device.

15. An analysis apparatus for analyzing an impurity in a gas, according to claim 10, further comprising a shifting device configured to shift at least one of said first and second measuring devices.

16. An analysis apparatus for analyzing an impurity in a gas, according to claim 12, wherein said supply mechanism is configured to supply said gases into said first and second cells at identical flow rates.

17. An analysis apparatus for analyzing an impurity in a gas, according to claim 12, further comprising a converting device for converting data measured with said first and second measuring devices into digital signals.

18. An analysts apparatus for analyzing an impurity in a gas, according to claim 12, wherein said determination mechanism multiplies data measured with one of said first and second measuring devices by a coefficient corresponding to a ratio of light powers of said first and second beams.

19. An analysis apparatus for analyzing an impurity in a gas, according to claim 18, further comprising a shifting device configured to shift at least one of said first and second measuring devices, wherein said determination mechanism determines said coefficient based on the ratio of the light powers of said first and second beams after shifting by said shifting device.

20. An analysis apparatus for analyzing an impurity in a gas, according to claim 12, further comprising a purge device configured to cover light paths from said light irradiating source to said first and second measuring devices, said purge device comprising a gas having no optical absorption in a range of wavelength to be measured.

21. An analysts apparatus for analyzing an impurity in a gas, according to claim 12, wherein said light irradiating source comprises a semiconductor laser.

22. An analysts apparatus for analyzing an impurity in a gas, according to claim 12, wherein:

said first cell is configured to contain a matrix gas and said impurity; and said second cell is configured to contain said matrix gas.

\* \* \* \* \*